US009250193B2

(12) United States Patent
Smith

(10) Patent No.: US 9,250,193 B2
(45) Date of Patent: Feb. 2, 2016

(54) GEMSTONE SPARKLE ANALYSIS

(75) Inventor: James Gordon Charters Smith, Buckinghamshire (GB)

(73) Assignee: De Beers UK Ltd., London (GB)

(*) Notice: Subject to any disclaimer, the term of this patent is extended or adjusted under 35 U.S.C. 154(b) by 667 days.

(21) Appl. No.: 13/575,067

(22) PCT Filed: Jan. 26, 2011

(86) PCT No.: PCT/GB2011/050122
§ 371 (c)(1),
(2), (4) Date: Oct. 3, 2012

(87) PCT Pub. No.: WO2011/092493
PCT Pub. Date: Aug. 4, 2011

(65) Prior Publication Data
US 2013/0016210 A1   Jan. 17, 2013

(30) Foreign Application Priority Data

Jan. 26, 2010 (GB) .................................. 1001236.7
Jan. 26, 2010 (GB) .................................. 1001237.5

(51) Int. Cl.
G01N 21/87 (2006.01)
G01N 33/38 (2006.01)
G01N 21/55 (2014.01)

(52) U.S. Cl.
CPC .............. G01N 21/87 (2013.01); G01N 33/381 (2013.01); G01N 21/55 (2013.01); G01N 2201/0634 (2013.01)

(58) Field of Classification Search
CPC ........................... G01N 11/022; G01N 11/024
USPC ....................................................... 348/135
See application file for complete search history.

(56) References Cited

U.S. PATENT DOCUMENTS 6,239,867 B1* 5/2001 Aggarwal ..................... 356/30
7,667,833 B1* 2/2010 Diver ............................ 356/138
(Continued)

FOREIGN PATENT DOCUMENTS

CH            700695 A2    9/2010
CN         101144704 A     3/2008
(Continued)

OTHER PUBLICATIONS

Chinese Office Action dated Oct. 10, 2014 for corresponding Chinese Application No. 2011800158607 and English translation.
(Continued)

*Primary Examiner* — Mehrdad Dastouri
*Assistant Examiner* — Jimmy S Lee
(74) *Attorney, Agent, or Firm* — Renner, Otto, Boisselle & Sklar, LLP

(57) ABSTRACT

A system is described for obtaining images of a gemstone, and performing quantitative analysis on the images to obtain measures of properties of the gemstone. The system comprises a support structure for supporting the gemstone at an observation position. An illumination structure is arranged to illuminate the gemstone. The illumination structure comprises a plurality of radially dispersed directional light sources directed towards the observation position, the support structure and illumination system being rotatable relative to one another around a rotation axis so that the gemstone can be illuminated by one or more of the directional light sources at each of a plurality of rotational positions, the axis of rotation being normal to a selected facet of the gemstone. An imaging device is directed towards the gemstone for obtaining images of the gemstone at each of the rotational positions, the imaging device having an imaging axis parallel to or coincident with the axis of rotation. An image processor is provided for identifying sparkle regions in the images corresponding to reflections from individual light sources by individual facets and providing a quantitative measure of the gemstone on the basis of porperties of the sparkle regions.

30 Claims, 4 Drawing Sheets

(56) References Cited

U.S. PATENT DOCUMENTS

| | | | |
|---|---|---|---|
| 8,065,314 B2* | 11/2011 | Prakash et al. | 707/758 |
| 8,169,531 B2* | 5/2012 | Chang et al. | 348/345 |
| 2009/0028424 A1* | 1/2009 | Sato et al. | 382/162 |
| 2009/0153835 A1* | 6/2009 | Sasian et al. | 356/30 |
| 2010/0086179 A1* | 4/2010 | Verboven et al. | 382/108 |
| 2010/0111354 A1* | 5/2010 | Hornabrook et al. | 382/100 |

FOREIGN PATENT DOCUMENTS

| | | | |
|---|---|---|---|
| CN | 101263381 A | | 9/2008 |
| EP | 1 319 942 A1 | | 6/2003 |
| EP | 1319942 A1 | * | 6/2003 |
| EP | 1 764 610 A1 | | 3/2007 |
| EP | 2 318 824 A1 | | 5/2011 |
| GB | 2462121 A | | 1/2010 |
| JP | 2002-500354 | | 1/2002 |
| JP | 2003-194725 | | 7/2003 |
| WO | WO 99/34197 A1 | | 7/1999 |
| WO | 2007/059090 A1 | | 5/2007 |
| WO | 2010/010375 | | 1/2010 |
| WO | WO 2010010375 A1 | * | 1/2010 |

OTHER PUBLICATIONS

International Search Report for corresponding International Application No. PCT/GB2011/050122 mailed May 22, 2012.

British Search Report for corresponding UK Application No. GB1001236.7 dated May 16, 2011.

International Preliminary Report on Patentability for corresponding International Application No. PCT/GB2011/050122 mailed Jul. 31, 2012.

* cited by examiner

GEMSTONE SPARKLE ANALYSIS

The present invention relates to an apparatus and method for viewing and analysing gemstones. In particular, although not exclusively, the invention relates to an apparatus and method for viewing a mark inscribed on the surface of the gemstone and quantifying the play of light within a gemstone.

The beauty or attractiveness of gemstones, and in particular diamonds, is considered to be directly related to how the stones interact with light. This interaction is known as the "play of light" and incorporates properties such as brilliance, fire and scintillation displayed by the stone. Brilliance relates to the intensity and contrast of light returned by the stone to the observer, fire relates to the amount of dispersed light returned by the stone and scintillation relates to the incidence of light flashes visible to the observer as the stone is moved relative to a light source.

Recently the practice of marking gemstones with brand marks, identification numbers, and/or marks conveying other information regarding the gemstone has become more widespread. Marks may be applied to stones using a variety of methods, such as for example those described in WO 98/52774. The marks can be applied so that they do not detract from the value or appearance of the gemstone. This means that the marks can be applied to facets such as the table of the stone. Such marks are typically inscribed to a depth of up to about 0.05 μm into the stone.

It would be advantageous to provide a reliable instrument that would allow the user to capture image data of the gemstone displaying the properties that make up the play of light and the inscribed mark and to make quantitative measurements of these properties in some way.

There are a number of viewers currently available that can be used to view play of light in gemstones. One example of such a viewer is provided in WO 2001/14854. Further viewers can also be used to view marks inscribed in stones, and such a device is described in WO 99/34197 which provides means to view a magnified image of the gemstone and the mark, but does not provide a means of viewing the play of light in the stone. A further viewer is described in EP 1319942 which enables the display of both play of light and a mark. However, due to the difficulty in providing the correct lighting conditions to display the play of light and the mark, the gemstone must be moved from one part of the viewer to another to view these different attributes.

It is known that, in order to display the properties of brilliance, fire and scintillation, varied lighting conditions are required. For example, the level of dispersed light may be hidden by the high level of reflected white light of a very brilliant gemstone under some lighting conditions. Varied lighting conditions may be provided by movable annular lighting such as that employed in the BrillianceScope™ Analyzer that measures the light that is returned through the crown of a diamond when it is illuminated from 6 different angles in a controlled lighting environment. It has also been shown to be advantageous to use multiple directional light sources, such as that produced by a number of LEDs, particularly when displaying the fire and scintillation of a gemstone. EP 1319942 describes an apparatus for determining play of light of a gemstone using a highly symmetrical lighting pattern that can be rotated and whose intensity can be controlled to vary the lighting. This symmetrical lighting system emphasises the symmetry of the stone. However, it is also known that, although highly symmetrically cut stones provide a good predictability for good play of light, stones with a lesser degree of symmetry can give equally good play of light.

Similarly, U.S. Pat. No. 7,315,356 provides an apparatus for imaging the fire of a gemstone where the varied lighting is provided by a symmetrical lighting pattern. It has been found that using a highly symmetrical lighting pattern does not provide adequate means for visual appreciation of the play of light for the majority of stones.

The invention is generally directed to a system for obtaining images of a gemstone, and performing quantitative analysis on the images to obtain measures of the properties of the gemstone. In particular, the invention is directed to a system of illuminating a gemstone at a plurality of rotational positions using one or more of a plurality of directional light sources. A diffuse light source may also be used. A facet of the gemstone (usually the table facet) should be normal to the axis of rotation. An axial light source should be arranged to direct light along the axis of rotation. An imaging device may be directed towards the gemstone, so that an imaging axis is coincident with the axis of rotation.

Images may be obtained at a range of rotational positions when the gemstone is illuminated by one or more of the directional light sources, axial light source and/or the diffuse light source. Analysis of these images may include identifying bright patches ("sparkles") in the images corresponding to reflections from individual light sources. The number, size, brightness, shape, distribution, contrast, symmetry, and/or variation with rotational position of the sparkles may be used in determining the property of the gemstone. Knowledge of the distribution of light sources may be used to complement the image contents to determine properties of the gemstone.

In accordance with one aspect of the present invention there is provided a system for obtaining images of a gemstone, and performing quantitative analysis on the images to obtain measures of properties of the gemstone. The system comprises a support structure for supporting the gemstone at an observation position. An illumination structure is arranged to illuminate the gemstone. The illumination structure comprises a plurality of radially dispersed directional light sources directed towards the observation position, the support structure and illumination system being rotatable relative to one another around a rotation axis so that the gemstone can be illuminated by one or more of the directional light sources at each of a plurality of rotational positions, the axis of rotation being substantially normal to a selected facet of the gemstone. An imaging device is directed towards the gemstone for obtaining images of the gemstone at each of the rotational positions, the imaging device having an imaging axis parallel to or coincident with the axis of rotation. An image processor is provided for identifying sparkle regions in the images corresponding to reflections from individual light sources by the gemstone and providing a quantitative measure of the gemstone on the basis of properties of the sparkle regions. The sparkle regions may correspond to reflections from individual light sources by individual facets of the gemstone.

The plurality of light sources may be located at a series of discrete inclination angles compared to the axis of rotation, and at polar angles chosen around the axis of rotation such that the imaging system does not possess rotational symmetry. The light sources at successive inclination angles advance in polar angle by a constant amount, optionally about 137.5°.

The analysis of the images may include using the number, size, brightness, shape, distribution, contrast, symmetry, and/or variation with rotational position of the sparkle regions in determining the measure of the gemstone.

The illuminating structure may include a diffuse light source and/or an axial light source configured to direct directional light along the imaging axis towards the gemstone.

The system may be configured to obtain images at a range of rotational positions when the gemstone is illuminated by one or more of the directional light sources, axial light source and/or the diffuse light source. The system may be configured to obtain a first sequence of images of the gemstone illuminated only by the axial light source at different rotational positions, and/or a second sequence of images of the gemstone illuminated only by the diffuse light source at different rotational positions, and/or a third sequence of images of the gemstone illuminated by each and/or all of the directional light sources at different rotational positions.

The first and/or sequence may comprise a few images (e.g. eight) at angles separated by of the order of 45°, for example. The third sequence may include a few hundred images of the gemstone illuminated by all of the directional light sources, and/or a few hundred for illumination by each of the directional light sources individually.

The image processor may be configured to identify the selected facet from some or all of the obtained images (optionally just the images in the first sequence), identify the centre of rotation, and rotate and register all of the images to a common centre.

The image processor may be configured so that each image in the third sequence is segmented into distinct regions, and a region is labelled as a sparkle region when light is reflected into the imaging device from that region. When a sparkle region is identified in an image, a search may be made for that sparkle region in all other images in the sequence.

The system may be configured to record measurements of one or more of the following features for each sparkle region and use the measurements in the quantitative analysis of the stone:
  the size of the sparkle region;
  at least one property of the shape of the sparkle region;
  the orientation of the sparkle region relative to the centre of the stone;
  the range of polar angles and/or inclination angles of the directional light sources causing the sparkle region to appear in an image;
  the range of colours present in the sparkle region;
  the brightest RGB illumination values in the sparkle region;
  the uniformity of illumination throughout the sparkle region; and
  the extent to which the sparkle region matches a generic template.

The system may be configured to record measurements of one or more of the following features and use the measurements in the quantitative analysis of the stone:
  the total number of sparkle regions over a threshold size;
  the average size of the sparkle regions;
  the variance in size of the sparkle regions;
  the proportion of the stone having sparkle regions;
  the average brightness of the sparkle regions;
  the symmetry of a pattern made up of all of the sparkle regions;
  the correlation between illumination inclination angles of a sparkle region and a corresponding symmetrically placed sparkle region;
  the degree of contrast in the stone;
  the rate of change of the pattern of sparkle regions with change in illumination of the stone; and
  the fraction of sparkle regions exhibiting a range of colours above a threshold value.

The system may be configured to obtain an image of a mark on the selected facet of the gemstone from one or more images of the gemstone illuminated by the axial light source.

Some of the images of the gemstone may be combined to produce a video illustrating the play of light in the gemstone.

In accordance with another aspect of the present invention there is provided a system for producing a video illustrating the play of light in a gemstone. The system comprises a support structure for supporting the gemstone at an observation position. An illumination system, comprising a plurality of directional light sources directed towards the observation position, is arranged to illuminate the gemstone. The support structure and illumination system are rotatable relative to one another around a rotation axis so that the gemstone can be illuminated by one or more of the directional light sources at each of a plurality of rotational positions, the directional light sources being disposed at a range of tilt angles and polar angles relative to the axis of rotation. An imaging device is directed towards the gemstone for obtaining images of the gemstone at each of the rotational positions. The imaging device has an imaging axis parallel to or coincident with the axis of rotation. An image processor is configured to select some or all of the images and combine the images into a video. The image processor may be configured to select for the video images having well defined sparkle regions corresponding to reflections from individual light sources by the gemstone.

The system of may further comprise a spatially distributed array of near-axial light sources configured to direct light along or nearly along the imaging axis for assisting with alignment of the selected facet of the stone normal to the imaging axis.

The array of near-axial light sources may be operable independently or simultaneously, so that a specular reflection from one or more of the near-axial light sources entering the imaging device can be identified, and an inclination of the selected facet from normal to the imaging axis can be determined from an angular offset from the imaging axis of the light source from which the specular reflection is detected.

The system may be configured to operate each light source in the array sequentially until a specular reflection from the light source is captured in the imaging device.

Angular spacing between adjacent sources in the array may be less than or comparable with an angle subtended by an aperture of the imaging device.

In accordance with another aspect of the present invention there is provided an apparatus for aligning a gemstone for viewing a mark. The apparatus comprises an array of independently operable directional light sources for directing light towards a facet of the gemstone. Viewing means (e.g. a camera) are provided for viewing the gemstone along an imaging axis. Control means are provided to control the operation of the light sources so that, initially, all of the light sources are activated simultaneously and, subsequently, the light sources are activated in sequence. Adjustment means are provided to adjust the alignment of the gemstone when all of the light sources are activated simultaneously until a specular reflection from the facet of light emitted by at least one of the light sources is observed at the viewing means. The control means are further configured to stop sequential activation of the light sources when a specular reflection, from the facet, of light emitted by one of the light sources is observed at the viewing means so the mark can be viewed.

Knowledge of which light source provides the light that is specularly reflected into the viewing means enables the adjustment of the alignment of the diamond further so that light emitted by a central light source of the array is specularly reflected into the viewing means.

A support means for the gemstone may be provided to maintain its alignment relative to the viewing means and array of light sources once it has been identified which light source emits the light which is specularly reflected into the viewing means.

A processor may be configured to analyse images of the facet and identify automatically when a specular reflection is observed at the viewing means.

In accordance with another aspect of the present invention there is provided a method for obtaining a quantitative measure of a gemstone. The method comprises illuminating the gemstone with a plurality of directional light sources arranged at a variety of inclination angles and polar angles compared to a rotation axis which is substantially normal to a selected facet of the gemstone. The gemstone and plurality of directional light sources are rotated relative to one another about the rotation axis to a plurality of rotation positions. An image of the gemstone is obtained along a viewing axis at each rotational position. Sparkle regions are identified in one or more of the images, the sparkle regions corresponding to reflections from individual light sources by facets of the gemstone. A quantitative measure of the gemstone is calculated on the basis of measureable properties of the sparkle regions.

In accordance with another aspect of the present invention there is provided a method of viewing a mark on a facet of a gemstone. The method comprises viewing the facet along an imaging axis and illuminating the facet using, simultaneously, all of a spatially distributed array of directional light sources. The alignment of the gemstone is adjusted (if necessary) until a specular reflection from the facet of light emitted by at least one of the light sources is observed on the imaging axis. The facet is then illuminated using each of the light sources sequentially until a specular reflection, from the facet, of light emitted by the currently activated light source is observed on the imaging axis. The mark, illuminated by the currently activated light source, can then be viewed illuminated by the currently activated light source.

Some preferred embodiments of the invention will now be described by way of example only and with reference to the accompanying drawings, in which.

General Arrangement

Figure 1:
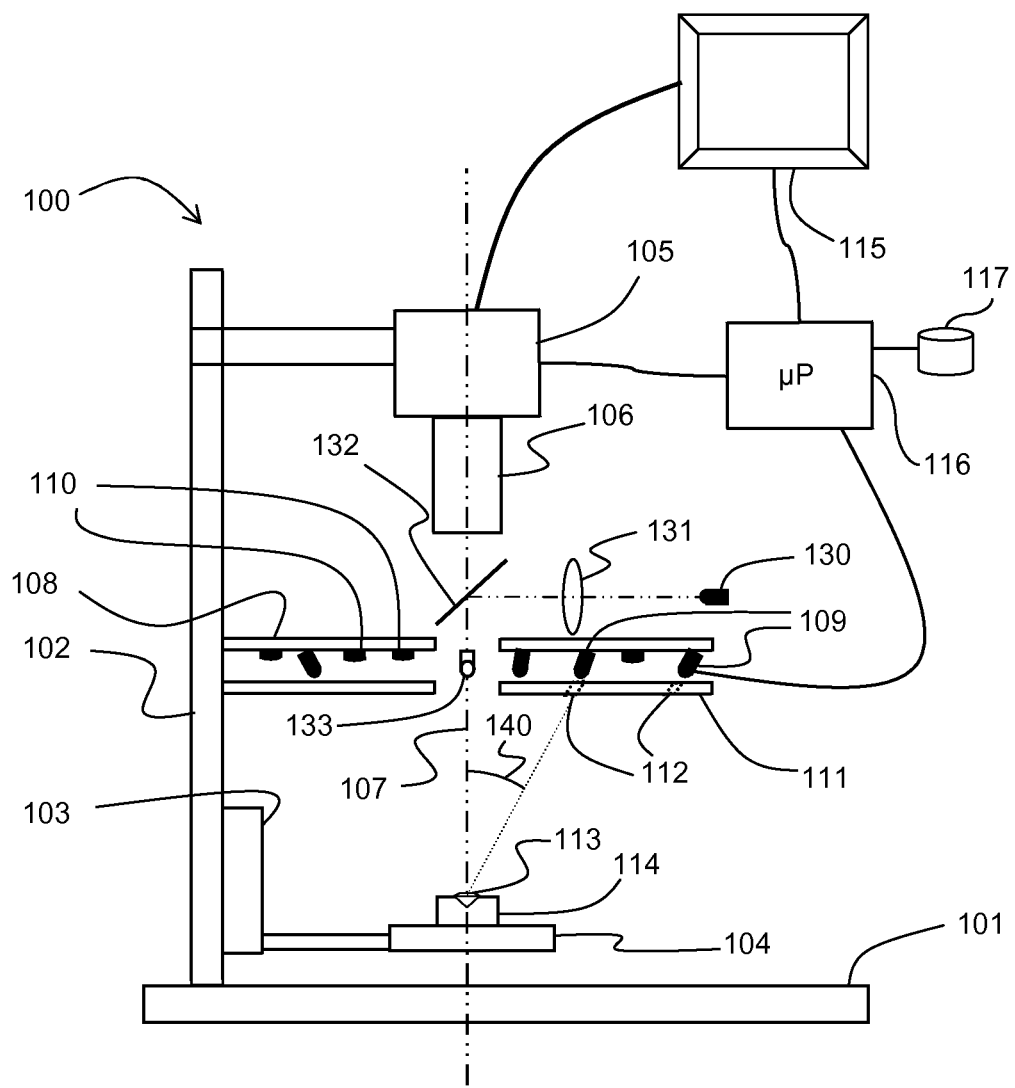
FIG. 1 is a schematic view of an instrument for obtaining images of a gemstone.

FIG. 1 shows a schematic diagram of an instrument for obtaining images of a gemstone 100. The structure of the instrument is formed by a base 101 and support member 102 which is generally perpendicular to the base 101. A linear slide 103 is movably mounted on the support member 102 so that it can move along the support member 102. A rotary table 104 is supported by the linear slide 103.

The surface of the rotary table 104 is optionally parallel to the base 101, and in normal operation the base 101 would be placed on a substantially horizontal surface such as the counter of a jewellery store. Thus references to horizontal and vertical in this description refer to directions parallel and perpendicular to the underside of the base 101.

An imaging device 105 such as a camera having a lens assembly 106 is mounted on the support 102 such that it points towards the rotary table 104 along an imaging axis 107, which should be parallel to the support member 102. The linear slide 103 thus allows the rotary table 104 to be moved towards or away from the imaging device 105 along the imaging axis 107. The imaging axis 107 is generally parallel to the axis of rotation of the rotary table 104.

The lens assembly 106 comprises a plurality of refracting elements and may be provided with internal mechanical motions that can alter the magnification between an object placed on the rotary table 104 and the imaging device 105, and adjust focus. Such lenses are commonly known as zoom or varifocal lenses. The imaging device 105 and the lens 106 may be a single module such as a Sony block camera combined with an auxiliary close up lens element. In an alternative embodiment or in addition, the imaging device 105 may be provided with more picture elements (pixels) than is required to produce images of acceptable quality so that the technique commonly known as digital zoom may be employed.

The instrument is also provided with an illumination structure 110, which may be characterised as combining two classes of lighting elements. One set provides a plurality of directional elements and a further set may provide a diffuse background. Any convenient light sources may be used. In one embodiment white light sources such as white Light Emitting Diodes (LEDs) are employed.

As shown in FIG. 1, the illumination structure 108 generally takes the form of a flat disc around the imaging axis 107, and comprises a set of directional LEDs 109 and a set of background LEDs 110, located above a diffuser 111. The diffuser 111 scatters the light propagating from the background LEDs 110 so as to provide a diffuse illumination to an object placed on the rotary table 104. Holes (or clear apertures) 112 in the diffuser 111 in front of each of the directional LEDs 109 allow directional illumination from the centre of each directional LED 109 to reach an object on the rotary table 104.

The illumination structure also includes an additional directional LED 130, relay lens 131 and beam splitter 132. The relay lens 131 forms a projected image 133, optionally at approximately unit magnification, of the additional directional LED 130. The beam splitter 132 allows a portion of this image to be projected along the imaging axis 107 so that the image 133 occupies the position in space that would have been occupied by the real source LED 130 had it actually been in the centre of the diffuser 111. This enables directional light to be directed along the imaging axis towards an object on the rotary table, and reflected back along the imaging axis into the lens 106 and imaging device 105 by a surface normal to the imaging axis 107. Other arrangements which enable this provision of directional light which can be retro-reflected back into the imaging device may also be envisaged. The axial source image 133 should be arranged so that it appears to be at the entrance pupil of the lens 106.

In use, a gemstone 113 such as a gem diamond is supported in a gemstone support 114 and placed on the rotary table 104 on the imaging axis 107. An image of the diamond 113 can then be formed in the imaging device 105 by the lens 106. The gemstone 113 can be rotated by rotation of the rotary table 104, and can be moved towards or away from the lens 106 by use of the linear slide 103. Images of the rotating diamond are obtained by the imaging device 105 and may be displayed on a screen 115 and/or sent to a processing device 116 associated with a storage medium 117. This enables a user to see magnified views of the gemstone 113 as it rotates, and this shows off the play of light in the diamond to great effect. The images can be stored in the storage medium 117 for future use.

The gemstone 113 will usually be a polished diamond, such as a round brilliant cut diamond, but it will be appreciated that other diamond cuts (or other gemstones) may also be viewed. The gemstone will generally have a major planar facet known as the table facet as its uppermost surface, and should be oriented so that this facet is as near to horizontal as possible. The normal to the table facet should be as close to 0° to the vertical (or the imaging axis 107) as is practical.

Alignment

In order to ensure that the normal to the table facet is as close to vertical as possible, a number of different approaches may be used, either individually or in combination. Initially, a levelling apparatus such as that described in GB 0911989.2 may be used. The method of GB 0911989.2 involves placing the gemstone into a vertically directed nozzle, increasing fluid pressure under the nozzle so that the gemstone is supported just above the nozzle on a cushion of air, and then slowly decreasing the fluid pressure so that the gemstone gradually settles back down into the nozzle. If this is done in a controlled manner it has been found that the table facet ends up level or nearly level. Further fine adjustment may then be carried out to complete the process, for example using a goniometer (not shown).

It may be that the images of the diamond shown on the display assist in ensuring that the normal to the table facet is parallel to the imaging axis 107. In particular, the gemstone 113 may be illuminated by the directional LED 130 acting as a "central" illumination source 133. When the gemstone is illuminated by this LED, light will be reflected directly back into the lens 106 when the table is perfectly aligned. If a mark is inscribed on the table, this mark should be clearly visible at such alignment. In addition, the retro-reflection indicating "perfect" alignment should be apparent from a bright spot of light in the images obtained by the imaging device 105 and displayed on the screen 115.

If the gemstone 113 is not perfectly aligned but the offset from perfect alignment is small, the specular reflection from the directional LED 130 will still pass through the aperture of the lens assembly 106, and an operator will be able to see from the images obtained by the imaging device how the orientation needs to be changed to get the alignment exact. If the offset is sufficiently large that the specular reflection does not pass into the imaging device 105, adjustment becomes a guess. Thus, unless the initial alignment is not very close to perfect, the operator is likely to have difficulty correcting any errors in alignment. This is a particular problem for mounted stones, or stones having a complex shape, as the initial levelling technique described in GB 0911989.2 may not be appropriate for such stones.

This alignment problem can be reduced if the angular size of the directional source 130 is increased. For example, if its diameter is increased by e.g. 5 times it will be 25× easier to find. However, the contrast of the table, and a mark inscribed on it, relies on the presence of specular reflection and, as the source becomes more diffuse, this contrast mechanism is lost. More specifically, in order for there to be appreciable contrast, the solid angle subtended by the source at the gemstone must be comparable or smaller than that subtended by aperture of the lens assembly 106.

One solution to this problem is to provide a large source made out of a plurality of smaller elements, each providing directional light. Then, there is a high or at least higher chance that light from at least one of the sources will be reflected into the imaging device 105. The sources may initially be illuminated all together to find a reflection, and subsequently activated individually, to assist with fine tuning of the alignment or to identify which of the sources is providing the contrast generating specular reflection. This approach is also useful just for viewing a mark on a gemstone, as well as for aligning the gemstone prior to obtaining a series of images as described below.

Figure 2:
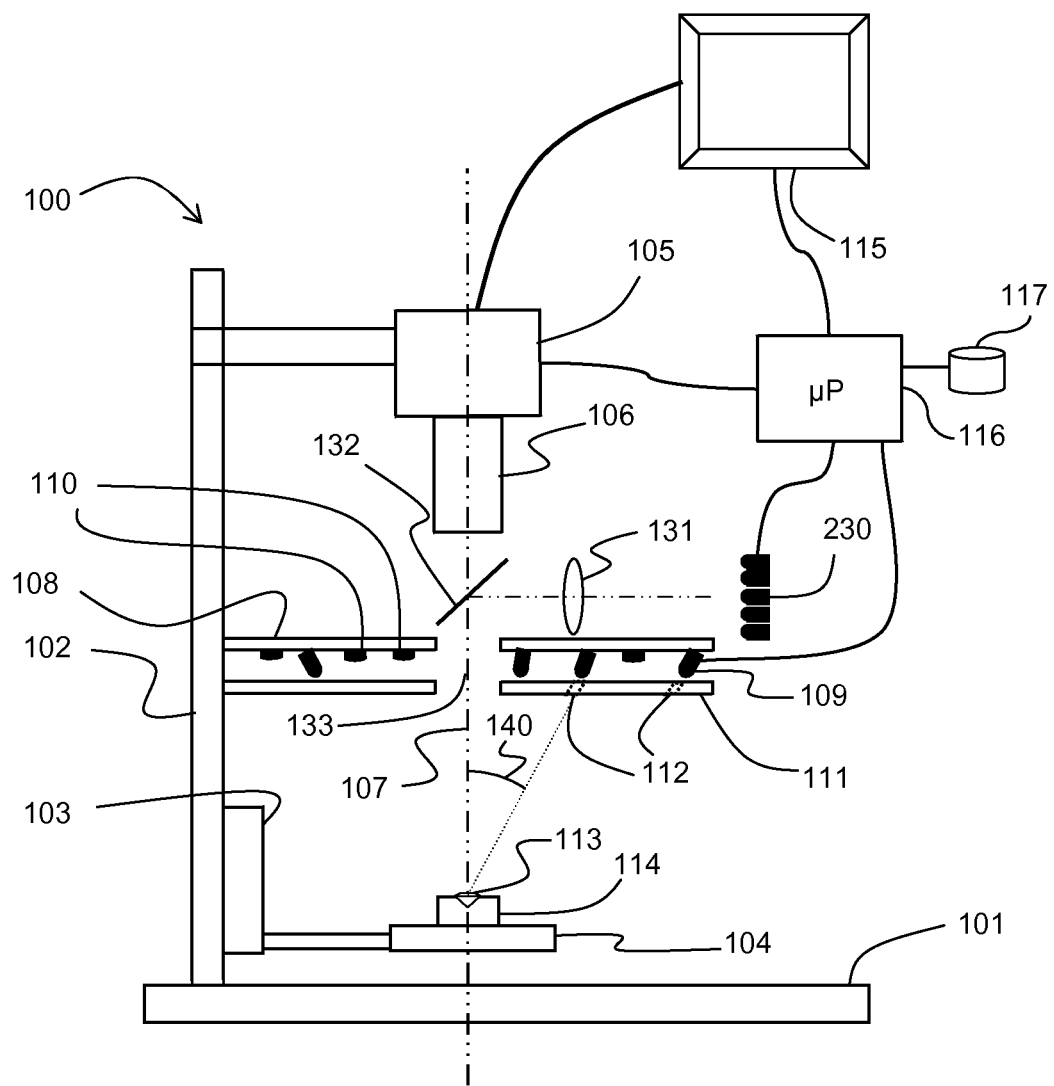
FIG. 2 is a schematic view of an instrument similar to FIG. 1 and including an array of LEDs to assist with alignment.

FIG. 2 shows an instrument generally identical to that of FIG. 1 but, instead of one directional LED 130, an array of e.g. 5×5 LEDs 230 is provided, placed close enough together so that effectively there are no gaps between the sources. The angular spacing between the sources should be less than or comparable to that subtended by the aperture of the lens assembly 106. An alignment process may then proceed as follows:

Initially, the operator causes all the sources to be illuminated (for example by pressing a button). Real time images of the gemstone 113 may be recorded by the imaging device 105 and displayed on the screen 115.

The operator aligns the stone 113 so that a reflection is seen on the screen. The larger area of the source array 230 makes this easier than the case where there is only a single point source.

In one alternative the operator may then cause the sources to be illuminated one at a time, for example for a period of 0.1 or 0.5 or 1 second each, and observe on a screen when an aligned image is seen. Alternatively the processing device 116 may analyse images from each source in the array 230, and identify which image corresponds to a direct specular reflection (in which cases the images may pass more often than once per second).

The operator may then cause the sequence to stop so that the mark is revealed. Alternatively, the processing device 116 may identify from the images when the mark is illuminated and carry out this step automatically. In a further alternative the changing light sequence need not be stopped, provided that the occasional clear view of the mark provides sufficient contrast.

Further minor adjustments may be carried out manually to improve the alignment. In particular, if it is known which of the light sources in the array 230 is emitting the light which is specularly reflected into the imaging device 105, it is simple to calculate what adjustment will need to be made to the alignment of the diamond to ensure that the table facet is normal to the imaging axis 107.

Optionally, the operator may then demonstrate the inscription to other parties such as a customer without them having to repeat the alignment procedure themselves. Since this may entail moving the apparatus it will be understood that suitable support means for the gemstone will be an element of the apparatus so as to avoid altering the relative alignment of the light source gemstone and viewing means.

It will be appreciated that this alignment method may also be used with instruments other than that shown in FIG. 2. Such instruments may provide illumination over a wider range of directions to allow an initial alignment to be made with ease, and then the range of directions that appear to be illuminated at any one time may be reduced to provide a clearer view of the mark. The 5×5 array described above may be include any suitable number of directional light sources, which need not be LEDs. Furthermore, a similar effect can be obtained by providing an LED array which is not effectively uniaxial with the imaging device 105: in order to see the mark, all that is required is a specular reflection.

Figure 3:
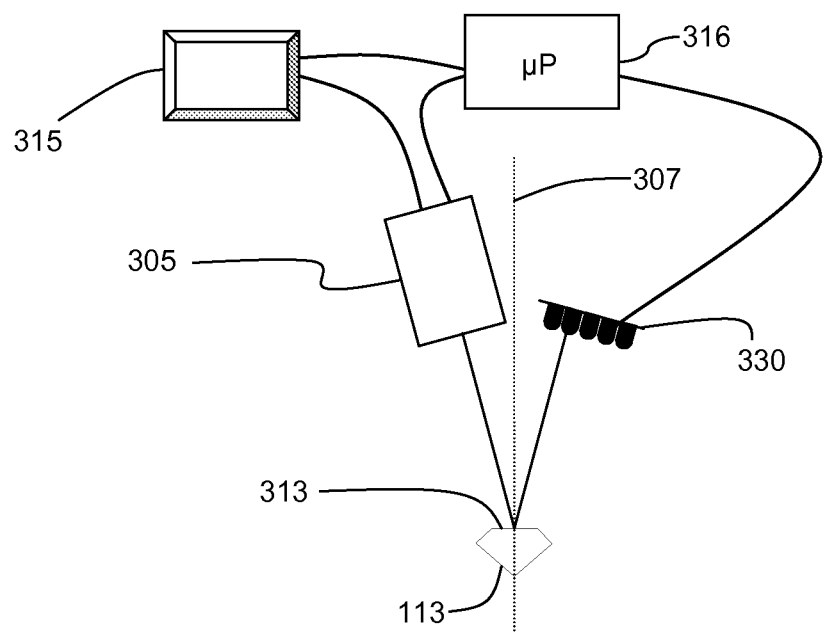
FIG. 3 is a schematic view of an alternative arrangement for aligning a gemstone.

Thus an arrangement as shown in FIG. 3 is also suitable for displaying a mark using a specular reflection. In this arrangement an array of directional light sources 330 and a camera 305 are provided at equal angles either side of a nominal axis 307 which should be a normal to the table facet 313 of the gemstone 113. The mark will be visible when a specular reflection is obtained in the camera 305. A processing device 316 may again control the operation of the light sources 330 and the camera 305, and images can be displayed on a screen 315.

Alternatively, the viewing means may be the human eye, possibly assisted by a magnifying lens or the like. Then each party might have to repeat the alignment process. In this case, support means for the gemstone need not be provided.

Further approaches may also be used. For example, the effect of the LED array 230, 330 of FIGS. 2 and 3 may be obtained by scanning a light beam over a reflecting surface (in place of the LED array) using, for example mirrors scanning at a rapid rate so that it appears that an extended region is illuminated. An initial alignment is made. The beam is then scanned with the same pattern, but much more slowly so that it now appears that only one spot of light is present. The operator may then stop the scan when the mark is seen clearly.

Control and Feedback

Returning to FIGS. 1 and 2, in operation it is advantageous for suitable control means such as the processing device 130 and suitable driver circuitry (not shown) to be able to have independent control of each of the directional LEDs 109. The brightness of each LED 109 may be adjustable either by controlling the current each draws, or by the technique of pulse width modulation. In addition the background LEDs 110 should have a similar control channel, common to all of the diffuse LEDS.

It will be appreciated that, although only one processing device 116 is shown, any number of processing devices to be used. Each may include or be associated with storage media 117 for storing the images, and/or memory (not shown) on which software may be stored.

The control means should also be able to control the motion of the linear slide 103 and the rotary table 104 to alter the relative position of the gemstone 113 and the lens 106. Motion of the linear slide constitutes a focus adjustment.

The control means should also have control over the operation of the imaging device 105 and the lens 106. Without limitation, these controls would cover the aperture stop of the lens 106, the exposure time of the imaging device 105 required to obtain each individual image and the gain, colour balance, contrast and brightness and any image sharpening provided in the imaging device 105. It may be that the lens 106 is provided with a focus adjustment that can be controlled automatically by the imaging device 106 or by the control means.

Care may be taken to ensure that the imaging device produces images where the signal is linearly proportional to the light level to simplify quantitative measurements. Images could be captured and stored in for example .bmp and .jpg formats on a hard disk either associated directly with the microprocessor or on a network.

Image data produced by the imaging device 105 may be displayed directly on a screen 115, such as a flat panel video monitor integrated into a housing (not shown) of the apparatus. For example, images of the gemstone 113 could be viewed simultaneously by a customer and a sales-person concerned with the potential purchase of the gemstone 113. A sequence of images obtained by the imaging device 105 may be viewed on the screen 115 as a video. Alternatively or in addition, It would be useful for some feedback to be provided so that the control means may make appropriate adjustments in order to obtain an attractive image sequence or video beneficial to the sales process. In its simplest form the sales-person could provide the feedback by evaluating the images and making adjustments to the various controls.

However it is preferable that the feedback is provided within the apparatus so that, once a start stimulus has been supplied, the apparatus carries out a predefined demonstration without further intervention. The apparatus may analyse the image data generated by the imaging device 105, by capturing image frames into computer memory (not shown) using a frame grabber or by direct use of an imaging device that produces a digital video signal. The image may be analysed and modified by data analysis and processing means. The displayed image may be of the original image data or that captured and modified by the data processing means (not shown).

As an example, and without limitation, the data processing means may split the image into separate red, green and blue channels, and calculate a histogram for each channel. The histogram may be used to identify the range of light levels apparent in each channel. These histograms may be compared with target values and used to adjust, for example the lighting level using either the directional or diffuse LEDs 109, 110. Further data processing may be used to identify the region of the image occupied by the gemstone 113, and if the image size were, for example too small, the control means may adjust the zoom setting of the lens 106 to provide more magnification.

Illumination

The dual arrangement of directional LEDs 109, together with background LEDs 110 and diffuser 111, assists in displaying and analysing the play of light in the gemstone. The directional LEDs 109, 130 act as "point sources" illuminating the gemstone 113. Light reflected from these point sources into the imaging device 105 will appear in the image of the gemstone 113 as scintillations and will cause the gemstone to appear to "sparkle". Light from the directional LEDs 109 will also be reflected out of the instrument and directly towards the observer, who will see the gemstone 113 sparkling both in the image on the screen 115 and directly "in the flesh".

If the gemstone 113 is illuminated only by the directional LEDs 109, it can sometimes appear as a generally dark image with a few spots of light. The background LEDs 110 and diffuser 111 provide a diffuse light that illuminates the whole of the gemstone 113 so that it appears much brighter in the image displayed on the screen 115. The combination of the two lighting effects results in a much more attractive image of the gemstone 113.

It will be understood that the diameter of the holes 112 in the diffuser 111 will have an effect on the apparent position of the light sources of the directional LEDs 109. These holes may be smaller in diameter than the directional LEDs, in which case the sources will appear to be located at the holes rather than at their real positions. Further optical elements may be provided between the directional LEDs 109 and the gemstone 113. One effect of these elements will be to alter further the apparent position of the directional LED sources.

As an alternative, the directional LEDs 109 may be of the surface mount type without lenses since this simplifies the manufacture of the illuminator. The background LEDs 110 could also be surface mount LEDs identical to those used for the directional LEDs 109, all mounted on one circuit board.

In another alternative, singlet lenses could be mounted over each hole 112 with their curved surfaces uppermost and placed so that the central ray (i.e. that ray that would illuminate the centre of the gemstone 113) of the LED source 109 meets the upper surface at close to normal incidence so that an undistorted beam is projected onto the gemstone 113.

Figure 4:
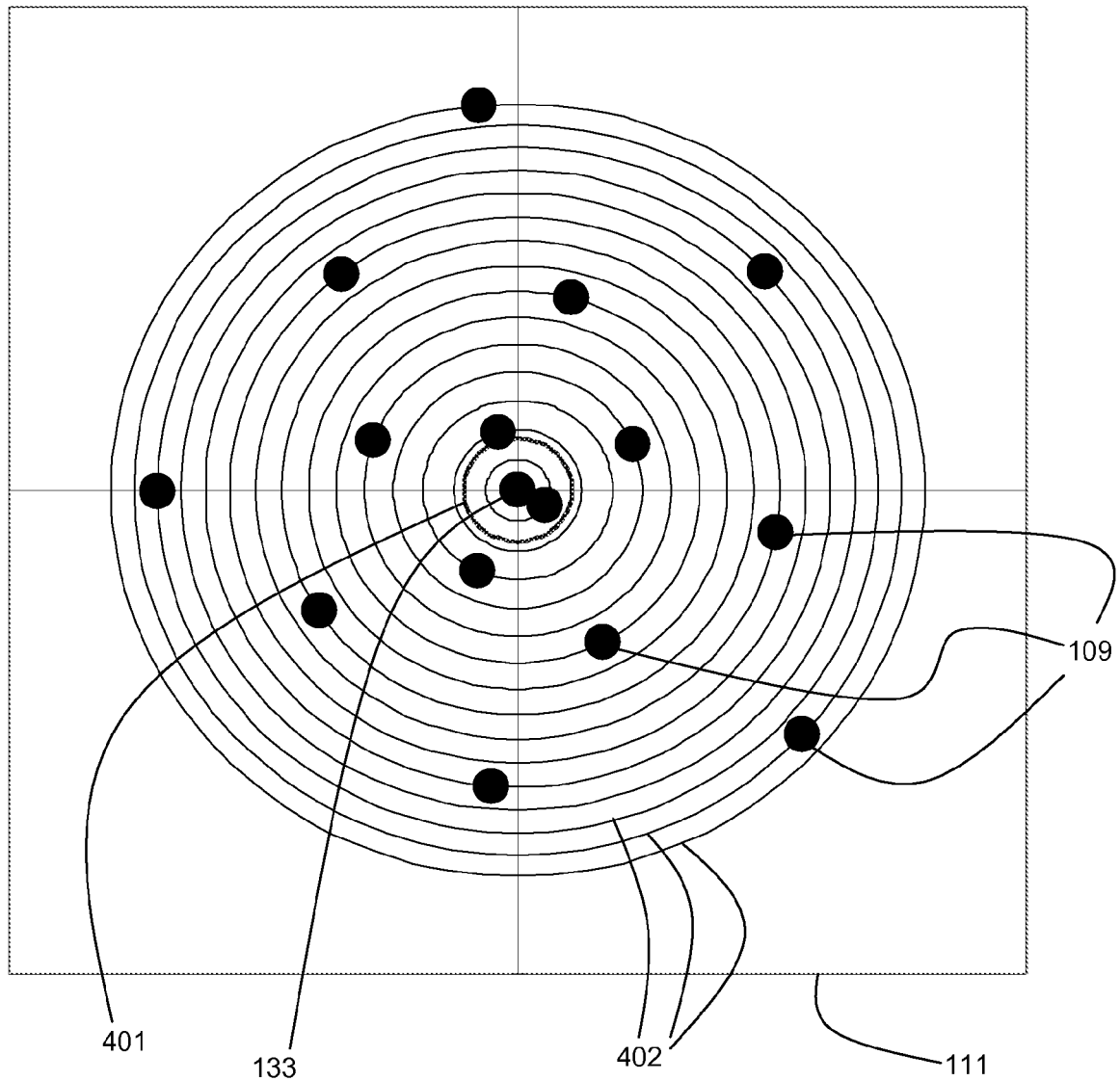
FIG. 4 is a schematic view of an arrangement of directional light sources.

FIG. 4 which shows, in schematic form, one possible arrangement of the underside of the diffuser 111 and the directional sources defined by the LEDs 109 seen through apertures 112 in the diffuser 111. A circle 401 in the centre of the figure represents the hole in the centre of the disc through which light from the lens 106 passes, and defines a region where it is not possible to place source LEDS directly without introducing beam splitters or similar.

A set of nested approximately circular curves 402 represent the loci of a series of discretely increased inclination angles 140. An inclination angle 140 is the angle made between the imaging axis 107 and a ray of light travelling from the LED 109 to the table facet of the gemstone 113, as shown in FIG. 1. It will be noted that the apertures 112 (and LEDs 109) also have a finite size and do not act as perfect point sources.

In this arrangement it can be seen that one LED 109 is arranged on the circle 402 for each discrete increase in inclination angle 140. The LEDs 109 are arranged so that each successive LED 109 is advanced in phase (also known as polar angle) by approximately 137.51°, an angle commonly referred to as the golden angle. This angle, which is encountered in natural growth forms such as in spiral phyllotaxis, ensures that successive source LEDs 109 are arranged reasonably uniformly about an axis, while ensuring that no simple symmetries, such as 4-fold or 8-fold, are present in the lighting arrangement that might emphasise the optical symmetry of the diamond. There may be any number of directional LEDs 109, but a typical number may be in the range 10-40. Embodiments with 16, 23 and 30 directional LEDs 109 have been tried. Similarly, the background LEDs may range in number between about 10 and about 40.

It will be understood by those skilled in the design of optical instrumentation that the criterion for the observation of a reflection should properly take into account the convolution of both the source LED aperture 109 and the optical aperture of the lens 106, but in practice this elementary treatment, which only considers the illumination of principal or chief ray provides sufficient guidance to assemble an apparatus according to the invention.

Although the use of the golden angle in the arrangement of the directional LEDs is effective in producing a balanced natural illumination, it will be appreciated that other arrangements are also possible, and apparatus may be assembled with any arrangement of the directional LEDs. For example a random or arbitrary phase for each successive ring may be employed.

Image Sequencing and Analysis

As discussed above, the directional LEDs are set out in a spiral arrangement with an angular advance of 137.51°. This arrangement provides an apparently random and approximately uniformly distributed set of sources but with a known underlying structure. In general each directional source has an inclination angle 140 to the vertical axis 107 and a polar angle representing a rotation about the vertical axis. The origin of the polar angle is arbitrary but may be defined with respect to the apparatus.

The initial position of the gemstone 113 defines an origin for the polar angle. If the gemstone 113 has been placed randomly this position is arbitrary. In one approach the gemstone 113 may be placed so that an inscription on the table of the gemstone 113 is aligned in a predefined way. One alternative is that the inscription is aligned naturally so that for example any text appears horizontal when the image is viewed on the screen 115.

It will now be understood that the rotary stage 104 introduces relative movement between the gemstone 113 and a given source 109 that may be considered to be a change in polar angle of that source with respect to the gemstone 113. Thus a small rotation (for example ¹⁄₂₀₀ of a turn or 1.8°) provides a small movement of each source around the polar axis.

However the absolute change in the position of the source 109 depends also on the angle of inclination 140. Thus a source 109 close to the vertical axis 107 has virtually no movement while one further away has a greater movement. (This is analogous to the apparent motion of the stars. The (northern hemisphere) pole star remains stationary while the others appear to move around it on circles of increasing radius)).

It is also important to consider the effect of rotating the polar angle abruptly through an angle corresponding approximately to the angular increment of the spiral illuminator, in this case 137.51° or approximately 76 steps of a 200 step stepper motor. Viewing the sources 109 from the gemstone 113, the apparent effect is to move each source by a small change in inclination angle 140 rather than a large change in polar angle. It will now be appreciated that the effect on the appearance of the gemstone of moving the inclination angle of a source may be seen by comparing images corresponding to adjacent sources with these large steps in polar angle. If, as in an alternative embodiment, the sources were arranged to provide a uniform increase in inclination angle the effect of moving a source through a known constant angle may be obtained.

All the directional light sources should be calibrated so that they produce a standard signal level when illuminating a white diffuser. (This requires a longer than normal exposure time.) The exposure time should then be shortened so that, in images of the gemstone, none of the pixels are saturated so that accurate measurements of light level can be made. In an alternative embodiment the exposure times may be increased to produce brighter and more realistic images for video generation purposes.

Three sequences of images may be obtained (although it will be appreciated that the images may not necessarily be recorded in the order described below):

In a first sequence only the "axial" LED 130, 133 is illuminated so as to provide a clear image of the table facet of the gemstone 113. A few images (e.g. in the range 4-20) are recorded and stored, with the rotary table being rotated between each one. For example, eight images corresponding to angular increments of 0, 45, 90 135, 180, 225, 270 and 315 degrees of polar angle may be recorded. For the purposes of the following discussion, these may be described as axial (A) images. If eight are obtained, these may be numbered images A0 to A7.

In a second sequence only the background illumination 110 is activated, and images are obtained at the same angles as used for first sequence. If eight images are used, these may numbered B0 to B7 and may be described as background (B) images. (In fact these two sequences may be recorded during just one rotation of the stage, alternating the lighting. A final rotation step would bring the polar angle to 360°, which is equivalent to being back at the origin.

In a third sequence, all the directional LEDs 109 (but not the axial LED 130) are illuminated, and the gemstone rotated through a series of much smaller angles. This results in a set of images of the order of a few hundred. In one embodiment a total of 201 images may be captured, corresponding to increments of 1.8°. These may be labelled S0 to S200 and may be described as sparkle (S) observation images.

In an alternative embodiment a further much larger set of images (a few thousand) may be captured. For each of the angular positions used for the sparkle observation image sequence, an image may also be recorded for each of the directional LEDS 109 in turn.

If there are thirty directional LEDs 109 and 201 angular positions for sparkle observation images, this will result in 6,030 images in the larger set. These may be labelled R0-1 ... R0-30 to R200-1 ... R200-30 and may be described as research images. It will be understood that any given Sparkle (S) image is in essence a combination of the corresponding 30 Research (R) images. This is a time consuming exercise and may not be desirable for an instrument used in a production environment. One advantage of the method is that data that yields similar results (i.e. the S data) can be obtained in a much shorter time.

This completes the image capture phase. The stone may then be removed from the apparatus, with analysis and video generation carried out later. However, it will be appreciated that analysis may proceed straight away. As will be seen, reference to the research images is optional but, in some circumstances, it may be desirable to refer to specific research images. In this case it would be possible to capture further single research images as required.

Several analyses of the image data may be carried out and a video produced.

Qualitative and General Observations

In one alternative observations may be of a qualitative nature and assessments largely subjective, but serve to illustrate wide range of applicability of image data For example, individual A images may be observed. Clear image of an inscription on the table facet may be observed in such images, and the images may be found (subjectively, by observers) to be pleasing.

Similarly, individual B images may be observed. Some of these images show the general arrangements of the light distribution of the gemstone and the patterning within the gemstone and this pattern may be considered to be pleasing. In some gemstones, images B1 to B7 may show identical patterning with some minor variation compared with B0 (other than the trivial rotation) caused by slight inhomogeneities in diffuse lighting. The background images could be considered to be divided up of a number of regions which are hereinafter referred to as individual Sparkles. Thus for the purposes of this document, a sparkle is defined as a connected region of a diamond where all parts of that region behave in a similar way to an external illumination stimulus.

Thus the overall appearance of a diamond may be analysed by breaking the diamond up into a set of sparkles and considering how each region behaves, as well as the general arrangement of the sparkles which corresponds to the pattern the observer sees when looking at the diamond.

It will be noted that performing this analysis based on the background images alone would be a formidable task, as there is no easy way of drawing the boundaries of each Sparkle.

Most of the S images are largely dark, but contain a few bright patches corresponded to certain individual Sparkles in the B images once rotation is allowed for. Since the S images typically have approximately 10-30 distinct regions, individual sparkles can be more readily identified and then mapped into the B images to produce a map of sparkles for the stone. For the purpose of this document a sparkle observation is an instance of the observation of a particular sparkle in an S image. Typically, each sparkle will have a set of sparkle observations, and each observation has a number of properties, for example but not limited to the average Red Green and Blue level.

Examination of the R images shows similar results to the S images but with typically only one or two sparkle observations (if any) per image: some have none. The same information can be obtained from these images as from the S images but with the additional certain assignment of a specific light source to the sparkle concerned.

For the R and S images the sparkle observations correspond to the "scintillations" or "sparkles" or "flashes" seen within the diamond when it is placed in an environment provided with a number of localised light sources such as spot lights, chandeliers, candelabras or the like. Part of the attractiveness of the diamonds is the "play of light" that occurs as the diamond or the observer or the lights are moved relative to each other.

Furthermore the colours observed correspond to the attractive property of the diamond known as "fire" or dispersion of colours, the variation in the angle of refraction of light at inclined surfaces caused by the variation of refractive index with wavelength.

Quantitative Analysis.

One possibility which allows without limitation an analysis based on the insights derived above is to describe the diamond as consisting of a collection of sparkles, and to determine properties of each sparkle. The discussion which follows is based on a set of eight A and B images and 201 S images as described above.

Identification of the Centre of Rotation.

An image (x,y) co-ordinate system is set up relative to the bottom left hand corner of the image.

For each of the eight axial images A0-A7, the table facet is isolated by removing any other stray reflections from the image. The outline of the table is obtained, or alternatively the coordinates of the corners of the table are found. The centroid of the table is found.

The centre of rotation is determined from the average of the eight centroids. The residual motion is a result of an offset between the centre of the stone and centre of rotation. This can be found by a weighted average of the eight values, the weight values corresponding to the sine and cosines of the polar angles—an application of Fourier analysis.

Image Registration

Once the centre of rotation is known it is possible to calculate a transformation to rotate and register each image to a common centre, taken to be the centre of the image. All the images are thus remapped to remove the polar angle so that the stone appears stationary in the image sequence. Each image may be held in computer memory to facilitate manipulations Identification of Sparkles and Sparkle Observations Each S image is segmented into a number of distinct regions corresponding to individual sparkles. Starting with the first sparkle observation image (S0) a single sparkle is identified and labelled. All the other images are checked to see if the same sparkle appears. Generally speaking, correspondences are found in images adjacent in the sequence and those separated by about 76 frames corresponding to jumps in inclination of the sources. A best estimate of the sparkle outline is recorded and applied to each image and also drawn onto a copy of a background image.

For each sparkle observation the average Red, Green and Blue values (RGB values) are recorded together with a measure of their variability within a sparkle, for example their interquartile ranges or standard deviations.

At the completion of the process, all of the illuminated regions of the background image should have been identified, but there may be some dark regions that were not seen. These correspond to regions that do not return light and are generally detrimental to the overall appearance of the diamond. However, the extent of these regions depends on the range of angles of inclination 140 provided in the apparatus. A range of 0° to 40° is provided in one embodiment, but this may be extended to an upper level of 45°, 50°, 55° or 60°, or even further to 90°, although this makes the apparatus rather cumbersome. Instead it may be better to extend the diffuse lighting to a larger angle of inclination and confine the directional LEDs 109 to regions of low inclination where the sparkle observations are concentrated.

The Analysis of a Single Sparkle

Without limitation the following features may be calculated for a single sparkle.

- Its size (either absolute in pixels which may be calibrated in mm or its size as a percentage of the stone area)
- Other properties of its shape such as long and thin or more uniform in shape.
- Its orientation (relative to the centre of the stone—for example does it point outwards like the spoke of a wheel?).
- The range of polar angles and/or inclination angles over which it was observed. These correspond to how quickly the appearance of the stone changes as it is moved.
- The range of colours seen in the sparkle corresponding to a measure of "fire" if the stone.
- The brightest RGB values over the observation set.
- The uniformity of illumination over the sparkle (which is related to polishing quality and the presence of inclusions.
- The inclination angle of the source that illuminated it. Thos may be known directly if the R images were used but it may also be estimated from the S image data. If the sparkle was seen over a wide range of polar angles it came from a source of low inclination. If it is only seen in a few frames it came from a large angle of inclination. Further inferences about the source may be determined by recognising that for many facets, and in particular the major facets that make up the well known "arrows pattern", the source will have a similar polar angle to that of the facet in a typical image or be diametrically opposed.
- A sparkle may be classified according to a generic template. For example it may form an arrow facet. The generic template may be chosen to match the general cut of the gemstone for example round brilliant, princess and heart shape.

Overall Properties of the Stones

Without limitation the following features may be calculated:

- The total number of sparkles (or sparkles over a certain threshold size).
- The average size of a sparkle, either absolute or relative to the size of the stone.
- The variance or variability of sparkle size.
- The fraction of the stone showing sparkles.
- The average brightness of the sparkles.
- The symmetry of the sparkle pattern. This is important for stones displaying optical symmetry.
- The correlation between the illumination angles of one sparkle and the angles for a symmetrically placed sparkle. For example the eight sparkles corresponding to the stems or heads of an arrow pattern.
- The degree of contrast in the stone. This considers whether adjacent sparkles are illuminated at the same time or different times.
- How quickly the overall sparkle pattern changes if the stone or the sources are moved.
- The overall fire of the stone, or for example the fraction of sparkles showing a given degree of fire.

Generation of a Video

In one alternative a video may be generated in real time by merely placing a stone in the apparatus as described, turning on a selection of lights setting the rotary in motion and capturing a sequence of images corresponding to the frames of a video.

Alternatively a video may be generated using data captured, namely the A, B and S image sequences. A convenient starting point are the images corrected for the centre of rotation and polar angle although it is not strictly necessary.

In one embodiment a storyboard is defined. This is a general description of the required video, frame by frame. For example the polar angle of each frame, the zoom level (or the desired size of the image in the frame) and the balance of lighting between directional (S images) background (B images) and if required axial illumination to reveal an inscription (A0 image). Other effects such as contrast or brightness adjustments may be specified. If the images were originally captured for analysis they will tend to be rather dull so some boosting of contrasting and adding in of highlights is fully justified. Other material may be introduced such as titles, music stock footage etc.

It will be understood that, once a storyboard is defined, it may be applied to many sets of images to produce videos of different stones to the same specification. Also it is possible to change a storyboard and regenerate new videos from the stored data to a new specification.

Videos often require the stone to be rotating, as it introduces variation lighting in a natural manner but it is obviously possible to produce a video where the stone is stationary and the lights moving using a similar method.

A video is generated by producing a series of frames which are then strung together and often heavily compressed by a video codec.

To generate an individual frame for a video the specification is derived from the storyboard. This will specify a polar angle for each frame. Unless the frames have been matched exactly to the captured sequence this polar angle will not correspond to one in the captured sequence. For example, suppose the required polar angle is 0.9°. The data set described has frame S0 captured at 0° and S1 at 1.8°. Thus an intermediate frame is required. This may be obtained by an interpolation procedure. The two frames S0 and S1 are rotated to the required angle of 0.9°. They both now show the diamond in the correct position but neither is illuminated exactly as they would be in the 0.9° position. However a very good estimate of the intermediate frame may be obtained by linear interpolation between the two frames—in this case such a simple average of the pixel intensities at each position. The situation for the B images is similar. B0 was captured at 0° and B1 at 45°. So in this case, after rotation to 0.9° the interpolation will make much more use of image B0 than B1. The same would apply to the A images, although these are not normally interpolated.

Once the three interpolated images are produced they may be mixed by simple arithmetic and any other adjustments made, to produce the final frame.

It will be understood that although the video frame is assembled by combining a number of separate elements the resulting images will be an accurate representation of how the gemstone would appear if it were viewed under the lighting conditions implicit in the storyboard. Thus the video frame and hence the complete video is realistic and legitimate or at least more realistic or legitimate than might be obtained, for example, by performing a ray-tracing simulation of a diamond with the same proportions to generate the video frame. Such simulations overlook the effect of factors such as polishing quality and the scattering of light within the stone.

The video may be put to any purpose. In one alternative the video may be provided to a customer who purchases the diamond. The customer may already have seen, for example in a jewellery store, the gemstone demonstrated on apparatus with a similar lighting arrangement to that herein described. Thus the video may serve as a reminder, memento, keepsake or the like and serve to reinforce the appreciation of their purchase.

EXAMPLE

An experimental apparatus broadly according to FIG. 1 was assembled. The base 101 was made of aluminium alloy plate and the support member 102 and other parts, from aluminium alloy extrusions, brackets and the like.

The linear slide 103 had 20 mm of travel and was driven by a linear actuator powered by a stepper motor and a microstepping driver module controlled via an RS232 interface from a IBM personal computer (PC).

The rotary table comprised a vacuum assisted mounting and levelling apparatus as described in GB 0911989.2 mounted on a further stepper motor with similar control means. The motor had a hollow shaft to facilitate the transfer of the vacuum pipes via a rotary swivel connector to the vacuum nozzle described in GB 0911989.2

The diffuser 111 was fabricated from clear 3 mm thick Macrolon polycarbonate sheet and was approximately 300 mm square. The diffusing effect was obtained by attaching two sheets of drawing film to the underside of the plate using 3 M spraymount adhesive. This composite plate was drilled with a plurality of holes approximately 5 mm in diameter, each hole inclined so that its axis was directed towards the centre of the rotary table 104, which was 120 mm below the diffuser. Sixteen directional white 5 mm diameter LEDs 109 (Marl model 110147-01 BC) with a 20 degree viewing angle were provided, arranged according to the spiral pattern illustrated in FIG. 2 and mounted directly into the holes in the diffuser plate.

A further twelve background LEDs 110 (Luxeon lumiled model LXHL-MWEC) were mounted in a circular pattern with a diameter of 110 mm on an aluminium alloy plate approximately 40 mm above the diffuser.

The beam splitter 132 and LED source 130 were provided so that a beam of light could be projected down the viewing axis 107 of the apparatus.

The directional LEDs 109 and axial LED 130 were controlled by the PC via a USB interface card model U3-LV by Labjack corporation of Lakeview, Colo. USA, and a proprietary interface that allowed each individual directional LED to be driven with a current of between 0 and 20 mA. The background LEDs were similarly controlled, and wired in series so that they could be driven with a controlled current of between 0 and 350 mA.

In another arrangement, the background LEDS 110 were also surface mount LEDS identical to those used for the directional LEDS 109, and they were all mounted on one circuit board. In this alternative embodiment 23 directional LEDS were provided and in a further embodiment 30 were used.

In one arrangement the LEDS were arranged so that the inclination angles between the (vertical) axis of the apparatus and a line drawn from the centre of the diamond to the source (i.e. position on the diffuser) increased uniformly for each source.

The camera 105 was a AVT Marlin colour camera which sent image information to the computer via a "Firewire" interface. In one embodiment the camera was programmed to send images comprising 800×800 pixels but other formats could be used. The camera had the desirable property that the physical spacing of the detector elements was identical in orthogonal vertical and horizontal directions providing "square" pixels. This simplifies subsequent geometrical transformations but it will be understood that imaging means with non-square pixels may be employed providing suitable corrections are made.

The camera was controlled by the PC allowing control of parameters such as gain exposure time. Care was taken to ensure the camera produced images where the signal was linearly proportional to the light level to simplify quantitative measurements. Images could be captured and stored in for example .bmp and .jpg formats on a hard disk either within the PC or on a network The .jpg formats offered a significant reduction in storage requirements (often 100:1) with negligible loss in image quality. The images were displayed on the monitor of the PC or others on the network.

The camera was provided with a lens assembly comprising a pair of doublet lenses and a circular mechanical iris stop and yielding a magnification of approximately −½. This lens formed a good quality image of the object onto the sensor of the camera. In one alternative the iris was set to a diameter of 8 mm. For a working distance of 120 mm this provided an object space Numerical Aperture of 0.033. This rays from the a given object point would be detected if they fell into a cone with a half angle of approximately 2 degrees.

The apparatus offered a field of view of approximately 7.5 mm×7.5 mm with no vignetting for an 800×800 pixel image which is easily large enough for round brilliant diamonds of up to 1 carat. Larger fields of view were possible. In an alternative embodiment a camera with more pixels could be provided so as to offer a larger field of view and/or higher resolution should this be desired.

The position of the axial source (which would be used to illuminate the table facet) was arranged so that it appeared to be at the entrance pupil of the lens. In practice, this matching was carried out empirically rather than by calculation, adjusting the relative position of the camera module and the diffuser/lens assembly until, as the turntable rotated, the specular reflection from the table facet of the gem diamond appeared to be illuminated uniformly without any obvious motion across the table. The apparatus was enclosed to exclude stray light sources.

In an alternative embodiment the PC was provided with a barcode reader or RF tag reader to allow data recorded to be associated with a particular diamond on a database, but these details could also be entered manually via a keyboard.

All the directional light sources were calibrated so that they produced a standard signal level when illuminating a white diffuser. (This required a longer than normal exposure time.) The exposure time was then shortened so that in diamond images none of the pixels were saturated so that accurate measurements of light level could be made. In an alternative embodiment the exposure times were increased to produce brighter and more realistic images for video generation purposes The apparatus was used to analyse the attractiveness and provide a video of a 0.67 carat round brilliant diamond inscribed with the Forevermark logo and a serial number using the following methods.

All the sources were switched on and a suitable exposure time was chosen. This would normally be a one off calibration process.

The details of the stone were recorded.

The diamond was cleaned and placed in the holder. The method described in GB 0911989.2 was used to level the diamond. Fine adjustments were made using a goniometer as described in GB 0911989.2. so that the table was illuminated uniformly by the axial LED. As a final check the rotary stage was turned by hand and the illumination remained constant.

The focus was set manually using the linear actuator to obtain the most attractive view of the inscription. There was sufficient depth of focus for the whole stone to appear in focus. Alternatively two focus positions could be defined, one for the mark and one for the stone as a whole.

The initial polar angle of the diamond was set so that the inscription was correctly oriented. This view defined the origin of the measurements and also corresponded to the image that would be used to reveal the inscription in the video. Since the image of the inscription, especially the serial number, is an important part of the video it is beneficial for this initial view to be accurately aligned to avoid having to introduce any degradation of the image by subsequent rotation in video production.

In alternative embodiments an arbitrary initial position was arbitrary or could be found by carrying out the method above automatically.

Three sequences of images were obtained using the method described above. In the first sequence only the axial LED was illuminated to provide a clear image of the table facet (which was approximately an octagon). Eight axial (A) images corresponding to angular increments of 0, 45, 90 135, 180, 225, 270 and 315 degrees of polar angle were recorded and stored as JPG images. These were numbered images A0 to A7.

In the second sequence only the background illumination was provided and eight background (B) images at the same angles as used for first sequence. These were numbered B0 to B7 These two sequences were recorded during just one rotation of the stage, alternating the lighting.

In the third sequences all the directional LEDs (but not the axial led) were illuminated and a total of 201 sparkle observation images were captured, corresponding to increments of 1.8°. These were labelled S0 to S200.

In addition, a much larger set of images (6,030) was captured. For each of the angular positions used for the sparkle observation image sequence a research (R) image was recorded for each of the 30 directional LEDS in turn. These were labelled R0-1 . . . R0-30 to R200-1 . . . R200-30. As explained above, a given S image is in essence a combination of the corresponding 30 R images.

The processing of the images was as described above. Qualitative observations were made. For example, image A0 was observed. A clear image of the inscription was (objectively) observed and was found (subjectively, by a number of observers) to be pleasing.

Image B0 was observed. This image shows the general arrangements of the light distribution of the diamond and the patterning within the diamond and this pattern was considered to be pleasing. Further examination of images B1 to B7 showed identical patterning with some minor variation compared with B0 (other than the trivial rotation) caused by slight inhomogeneities in diffuse lighting. It was observed that the background images could be divided up of a number of regions, referred to in the discussion above as sparkles (as previously discussed, a sparkle is defined as a connected region of a diamond where all parts of that region behave in a similar way to an external illumination stimulus).

Examination of the images S1-S200 showed that in general each image was largely dark but contained a few bright patches corresponding to certain individual Sparkles in the B images once rotation was allowed for. Since the S images typically had approximately 10 or 20 or 30 distinct regions it was clear that individual sparkles could be more readily identified and then mapped into the B images to produce a map of sparkles for the stone.

Examination of the R images showed similar results to the S images but with typically only one or two sparkle observation per image, and some with none. The same information could be obtained from these images as from the S images but with the additional certain assignment of a specific light source to the sparkle concerned.

The quantitative analysis of the images was carried out as described above.

A video was also generated from the images. The video had a duration of 20 seconds and was generated at frame rate of 30 per second requiring 600 frames in total. The stone completed one rotation and the inscribed mark was revealed in the final 5 seconds by fading up the A0 frame. The magnification was continuously increased through the sequence to give the impression of zooming into the inscription.

Once the frames were produced standard codecs were used to produce videos in a range of formats and payable on a range of computers and portable devices for publicity purposes.

Some scintillations were essentially a transition from dark to light (i.e. white) to dark again, but others could be characterised as a transition through the visible spectrum from blue to red or vice versa, the colours being most obvious at the blue and yellow—red ends of the spectrum. This is the phenomenon known as fire in the diamond trade.

It was found that many other attractive effects could be generated including but not limited to:

Reducing the lens aperture (for example to f/8 or f/11) to reduce the overall intensity of the light and increase the amount of "Fire" that could be observed in each scintillation.

Allowing the turntable to rotate slowly or come to rest as the inscription was revealed to produce a range of contrast effects as the light source is scanned across the entrance pupil of the lens.

It was also possible to introduce extra dynamic effects into the scintillation effect by switching the LEDs on and off at a suitable rate, or using LEDs that could display different colours. However these effects could be considered to be contrived or unnatural and might be best employed sparingly if at all.

It will be appreciated that variations from the above described embodiments may also fall within the scope of the present invention. For example, the system has been described with reference to a rotary table on which a diamond can be placed. It will be appreciated that the illumination structure and/or camera may be rotated relative to the diamond, instead of the diamond being physically rotated, although the results tend to be more aesthetically pleasing if the diamond itself is rotated. As a further alternative, the directional LEDs could be activated in sequence to provide the effect of a rotating illumination structure.

In addition, it will be appreciated that it may be possible to use additional directional LEDs instead of the background LEDs and diffuser, although this may affect the balance between scintillations and background illumination, which may be less aesthetically pleasing.

The directional light sources have been described as directional LEDs 109 located behind holes or clear apertures 112 in the diffuser 111. It will be appreciated that any suitable arrangement for providing directional light may be used. In one arrangement, directional light may be provided by LEDs (or any suitable light source) located behind collimating lenses. These lenses may be incorporated or moulded preferably onto the upper surface of the diffuser. Preferably the lenses should be arranged so that the ray of light that illuminates the centre of the diamond should meet the curved surface of the lens at normal incidence.

Furthermore, the apparatus has been described with a base and generally vertical support member. It will be appreciated that other arrangements will be available in practice, as long as the necessary rotations between diamond, illumination structure and camera can be achieved, and as long as the camera can be focussed on the diamond. In practice, the elements (including the viewing screen) may be incorporated into a single, stand-alone instrument. Such an instrument may still have a large opening through which the diamond can be observed directly, so that the diamond can be viewed simultaneously on the screen and "in the flesh".

The invention claimed is:

1. A system for obtaining images of a gemstone, and performing quantitative analysis on the images to obtain measures of properties of the gemstone, comprising:
    a support structure for supporting the gemstone at an observation position;
    an illumination system arranged to illuminate the gemstone, the illumination system comprising a plurality of directional light sources directed towards the observation position, the support structure and illumination system being rotatable relative to one another around a rotation axis so that the gemstone can be illuminated by one or more of the directional light sources at each of a plurality of rotational positions, the directional light sources being disposed at a series of discrete inclination angles relative to the axis of rotation, and at polar angles chosen around the axis of rotation such that the imaging system does not possess rotational symmetry;
    an imaging device directed towards the gemstone for obtaining images of the gemstone at each of the rotational positions, the imaging device having an imaging axis parallel to or coincident with the axis of rotation; and
    an image processor for identifying sparkle regions in the images corresponding to reflections from individual light sources by the gemstone and providing a quantitative measure of the gemstone on the basis of properties of the sparkle regions.

2. The system of claim 1, wherein light sources at successive inclination angles advance in polar angle by a constant amount.

3. The system of claim 2, wherein the constant amount is approximately 137.5°.

4. The system of claim 1, wherein the axis of rotation is normal to a selected facet of the gemstone.

5. The system of claim 1, wherein the sparkle regions correspond to reflections from individual light sources by individual facets of the gemstone.

6. The system of claim 1, wherein the analysis of the images includes using the number, size, brightness, shape, distribution, contrast, symmetry, and/or variation with rotational position of the sparkle regions in determining the measure of the gemstone.

7. The system of claim 1, wherein the illumination system comprises a diffuse light source.

8. The system of claim 1, wherein the illumination system comprises an axial light source configured to direct directional light along the imaging axis towards the gemstone.

9. The system of claim 1, configured to obtain images at a range of rotational positions when the gemstone is illuminated by one or more of the directional light sources, axial light source and/or the diffuse light source.

10. The system of claim 1, configured to obtain a first sequence of images of the gemstone illuminated only by the axial light source at different rotational positions, and/or a second sequence of images of the gemstone illuminated only by the diffuse light source at different rotational positions, and/or a third sequence of images of the gemstone illuminated by each and/or all of the directional light sources at different rotational positions.

11. The system of claim 10, wherein the first and/or sequence of images comprises a number of images in the range four to twenty, preferably eight.

12. The system of claim 10, wherein the third sequence of images includes between 100 and 500, preferably 201, images of the gemstone illuminated by all of the directional light sources simultaneously, and/or, for each if the directional light sources, between 100 and 500, preferably 201, images of the gemstone illuminated by that light source alone.

13. The system of claim 1, wherein the image processor is configured to identify the selected facet from some of the obtained images, identify the centre of rotation, and rotate and register all of the images to a common centre.

14. The system of claim 13, wherein the image processor is configured to identify the selected facet and the centre of rotation from the images in the first sequence.

15. The system of claim 10, wherein the image processor is configured so that each image in the third sequence is segmented into distinct regions, and a region is labelled as a sparkle region when light is reflected into the imaging device from that region.

16. The system of claim 15, wherein the image processor is further configured so that, when a sparkle region is identified in an image, a search is made for that sparkle region in all other images in the sequence.

17. The system of claim 15, configured to record measurements of one or more of the following features for each sparkle region and use the measurements in the quantitative analysis of the stone:
    the size of the sparkle region;
    at least one property of the shape of the sparkle region;
    the orientation of the sparkle region relative to the centre of the stone;
    the range of polar angles and/or inclination angles of the directional light sources causing the sparkle region to appear in an image;
    the range of colours present in the sparkle region;
    the brightest RGB illumination values in the sparkle region;
    the uniformity of illumination throughout the sparkle region;
    the extent to which the sparkle region matches a generic template.

18. The system of claim 15, configured to record measurements of one or more of the following features and use the measurements in the quantitative analysis of the stone:
    the total number of sparkle regions over a threshold size;
    the average size of the sparkle regions;
    the variance in size of the sparkle regions;
    the proportion of the stone having sparkle regions;
    the average brightness of the sparkle regions;
    the symmetry of a pattern made up of all of the sparkle regions;
    the correlation between illumination inclination angles of a sparkle region and a corresponding symmetrically placed sparkle region;
    the degree of contrast in the stone;
    the rate of change of the pattern of sparkle regions with change in illumination of the stone; and
    the fraction of sparkle regions exhibiting a range of colours above a threshold value.

19. The system of claim 1, configured to obtain an image of a mark on the selected facet of the gemstone from one or more images of the gemstone illuminated by the axial light source.

20. The system of claim 1, further configured to combine some of the images of the gemstone to produce a video illustrating the play of light in the gemstone.

21. A system for producing a video illustrating the play of light in a gemstone, comprising:
   a support structure for supporting the gemstone at an observation position;
   an illumination system arranged to illuminate the gemstone, the illumination system comprising a plurality of directional light sources directed towards the observation position, the support structure and illumination system being rotatable relative to one another around a rotation axis so that the gemstone can be illuminated by one or more of the directional light sources at each of a plurality of rotational positions, the directional light sources being disposed at a series of discrete inclination angles relative to the axis of rotation, and at polar angles chosen around the axis of rotation such that the imaging system does not possess rotational symmetry;
   an imaging device directed towards the gemstone for obtaining images of the gemstone at each of the rotational positions, the imaging device having an imaging axis parallel to or coincident with the axis of rotation; and
   an image processor for selecting some or all of the images and combining the images into a video, wherein the image processor is configured to select for the video images having well defined sparkle regions corresponding to reflections from individual light sources by the gemstone.

22. A method for obtaining a quantitative measure of a gemstone, comprising:
   illuminating the gemstone with a plurality of directional light sources arranged at a variety of discrete inclination angles relative to a rotation axis which is substantially normal to a selected facet of the gemstone, and at polar angles chosen such that the illumination does not possess rotational symmetry;
   rotating the gemstone and plurality of directional light sources relative to one another about the rotation axis to a plurality of rotation positions;
   obtaining an image of the gemstone along a viewing axis at each rotational position;
   identifying sparkle regions in one or more of the images, the sparkle regions corresponding to reflections from individual light sources by facets of the gemstone; and
   calculating a quantitative measure of the gemstone on the basis of measureable properties of the sparkle regions.

23. The method of claim 22, wherein the quantitative measure is calculated using the number, size, brightness, shape, distribution, contrast, symmetry, and/or variation with rotational position of the sparkle regions.

24. The method of claim 22, further comprising illuminating the image with a diffuse and/or axial light source configured to direct directional light along the imaging axis towards the gemstone, and further comprising obtaining images at a range of rotational positions when the gemstone is illuminated by one or more of the directional light sources, axial light source and/or the diffuse light source.

25. The method of claim 22, further comprising segmenting images obtained when the gemstone is illuminated by one or more of the directional light sources into distinct regions, and labelling a region as a sparkle region when light is reflected into the imaging device from that region.

26. The method of claim 25, further comprising, when a sparkle region is found in one image, searching for that sparkle region in all other images.

27. The method of claim 25, further comprising using measuring one of more of the following features for each sparkle region and using the measurements in determining the quantitative measure of the stone:
   the size of the sparkle region;
   at least one property of the shape of the sparkle region;
   the orientation of the sparkle region relative to the centre of the stone;
   the range of polar angles and/or inclination angles of the directional light sources causing the sparkle region to appear in an image;
   the range of colours present in the sparkle region;
   the brightest RGB illumination values in the sparkle region;
   the uniformity of illumination throughout the sparkle region;
   the extent to which the sparkle region matches a generic template.

28. The method of claim 25, further comprising measuring one of more of the following features and using the measurements in determining the quantitative measure of the stone:
   the total number of sparkle regions over a threshold size;
   the average size of the sparkle regions;
   the variance in size of the sparkle regions;
   the proportion of the stone having sparkle regions;
   the average brightness of the sparkle regions;
   the symmetry of a pattern made up of all of the sparkle regions;
   the correlation between illumination inclination angles of a sparkle region and a corresponding symmetrically placed sparkle region;
   the degree of contrast in the stone;
   the rate of change of the pattern of sparkle regions with change in illumination of the stone; and
   the fraction of sparkle regions exhibiting a range of colours above a threshold value.

29. The method of claim 22, further comprising obtaining an image of a mark on the selected facet of the gemstone from one or more images of the gemstone illuminated by the axial light source.

30. The method of claim 22, further comprising combining some of the images of the gemstone to produce a video illustrating the play of light in the gemstone.

* * * * *